United States Patent
Corbucci (10) Patent No.: US 7,647,103 B2
(45) Date of Patent: Jan. 12, 2010

(54) ADDRESSING PACEMAKER SYNDROME

(75) Inventor: Giorgio Corbucci, Cento (IT)

(73) Assignee: Medtronic, Inc., Minneapolis, MN (US)

( * ) Notice: Subject to any disclaimer, the term of this patent is extended or adjusted under 35 U.S.C. 154(b) by 1333 days.

(21) Appl. No.: 10/422,064

(22) Filed: Apr. 23, 2003

(65) Prior Publication Data

US 2004/0215268 A1 Oct. 28, 2004

(51) Int. Cl.
*A61N 1/362* (2006.01)

(52) U.S. Cl. .................................................. 607/9

(58) Field of Classification Search .................. 607/27, 607/14, 9; 600/515, 516
See application file for complete search history.

(56) References Cited

U.S. PATENT DOCUMENTS

| | | | | |
|---|---|---|---|---|
| 4,593,695 | A | * | 6/1986 | Wittkampf ..................... 607/27 |
| 4,951,667 | A | | 8/1990 | Markowitz et al. |
| 5,179,949 | A | | 1/1993 | Chirife |
| 5,228,438 | A | * | 7/1993 | Buchanan ..................... 607/18 |
| 5,312,445 | A | * | 5/1994 | Nappholz et al. ............... 607/9 |
| 5,395,397 | A | * | 3/1995 | Lindgren et al. ............... 607/9 |
| 5,514,164 | A | | 5/1996 | Mann et al. |
| 5,814,077 | A | | 9/1998 | Sholder et al. |
| 5,873,895 | A | | 2/1999 | Sholder et al. |
| 6,122,546 | A | | 9/2000 | Sholder |
| 2002/0161409 | A1 | | 10/2002 | Rouw et al. |
| 2004/0215268 | A1 | | 10/2004 | Corbucci |

OTHER PUBLICATIONS

Geiter, Henry B Jr., "LookSmart's FindArticles—Getting back to basics with permanent pacemakers, part II"; Nursing, Nov. 2004, <http://www.findarticles.com/p/articles/mi_qa3689/is_200411/ai_n9471352> accessed Apr. 12, 2006.*

"Persistent Dizziness", Postgrad. Med. J. 2002;78;692-693 (doi:10.1136/pmj.78.925.692-a) <http://pmj.bmjjournals.com/cgi/content/full/78/925/692-a#BIBL> accessed Apr. 12, 2006.*

Carol J. Van Orden Wallace, "Diagnosing and Treating Pacemaker Syndrome," Feb. 2001, vol. 21, No. 1, http://www.aacn.org/aacn/jrnlccn.nsf/c54ad59fdf5d6228882565a0006a1369/9e057e5f5bc91.

Vardas et al., "AAIR versus DDDR Pacing in Patients with Impaired Sinus Node Chronotropy: An Exhocardiographic and Cardiopulmonary Study," PACE, vol. 20, Jul. 1997, pp. 1762-1768.

Iliev et al., "Preserving Normal Ventricular Activation Versus Atrioventricular Delay Optimization During Pacing: The Role of Intrinsic Atrioventricular Conductio and Pacing Rate," PACE, vol. 23, Jan. 2000, pp. 74-83.

(Continued)

*Primary Examiner*—George R Evanisko
*Assistant Examiner*—Alyssa M Alter
(74) *Attorney, Agent, or Firm*—Stephen W. Bauer (57) ABSTRACT

In general, the invention is directed to techniques for detecting and addressing pacemaker syndrome. When a pacemaker detects a risk of pacemaker syndrome, the pacemaker paces one or more chambers of the heart to reduce the risk of pacemaker syndrome. One pacing technique is to apply ventricular paces, thereby reducing the delay between the atrial activation and the ventricular activation. Another technique, available to a patient who receives atrial pacing, is to decrease the atrial pacing rate.

29 Claims, 5 Drawing Sheets

OTHER PUBLICATIONS

Meine et al., "Relationship Between Atrioventricular Delay and Oxygen Consumption in Patients with Sick Sinus Syndrome: Relevance to Rate Responsive Pacing," PACE, vol. 22, Jul. 1999, pp. 1054-1063.

Mabo, "Lack of Physiological Adaptation of the Atrioventricular Interval to Heart Rate in Patients Chronically Paced in the AAIR Mode," PACE, vol. 14, Dec. 1991, pp. 2133-2142.

Schwaab et al., "AV Conduction with Atrial Rate Adaptive Pacing in the Bradycardia Tachycardia Syndrome," PACE, vol. 22, Oct. 1999, pp. 1502-1509.

Barold, "Optimal Pacing in First-Degree AV Block," PACE, vol. 22m, Oct. 1999, pp. 1423-1424.

Barold, S. Serge, "Indications for Permanent Cardiac Pacing in First-Degree AV Block: Class I, II, or III?", PACE, vol. 19, May 1996, pp. 747-751.

Chirife, R., MD et al., "Pacemaker Syndrome Without a Pacemaker. Deleterious Effect of First Degree A-V Block", Institute of Cardiology, National Academy of Medicine, Buenos Aires, RA.

* cited by examiner

ADDRESSING PACEMAKER SYNDROME

FIELD OF THE INVENTION

The invention relates to cardiac pacing systems, and in particular, to implantable pacing systems.

BACKGROUND OF THE INVENTION

A healthy cardiac cycle includes a period of passive filling of the heart during atrial and ventricular diastole, followed by atrial contraction, which forces blood through the atrioventricular valves into the ventricles. Following atrial contraction, the ventricles contract, expelling blood from the heart into the rest of the body.

Some patients have implantable pacemakers that deliver electrical stimuli or paces to the atria or the ventricles or both, causing the chambers to activate. In general, a pacemaker delivers paces to promote atrioventricular synchrony, i.e., to cause the atria and ventricles to contract in a cooperative and efficient fashion. In some circumstances, however, pacing fails to cause atrioventricular synchrony, and instead causes the atria and the ventricles to activate out of sequence at approximately the same time. The result is a phenomenon known as "pacemaker syndrome."

Activation of the atria and ventricles at substantially the same time causes the atria and ventricles to work against one another. Instead of ejecting the blood into the body, the ventricles force some blood backward through the atrioventricular valves and into the atria. As a result, a patient suffering from pacemaker syndrome generally experiences adverse effects due to reduced hemodynamic function of the heart, such as weakness, dizziness and shortness of breath.

BRIEF SUMMARY OF THE INVENTION

In general, the invention is directed to techniques for detecting and addressing pacemaker syndrome. A pacemaker has the capability to detect electrical signals generated by the heart. In a patient with pacemaker syndrome, the P-wave, which accompanies atrial activation, is superimposed on the T-wave, which accompanies ventricular repolarization. In other words, a T-wave of a patient with pacemaker syndrome does not occur substantially ahead of a P-wave in a successive cardiac cycle. Rather, the T-wave and P-wave overlap, or the T-wave precedes the P-wave by a brief time interval. When a pacemaker detects pacemaker syndrome, the pacemaker applies pacing therapy to the atria or ventricles or both to restore a satisfactory atrioventricular sequence.

A patient may be at risk of pacemaker syndrome in some circumstances and not at risk in others. Under ordinary operating conditions, the patient may not be at risk of pacemaker syndrome. The patient may be at risk, however, when the patient's heart rate increases. Further, some pacemakers are programmed to pace at a different rate depending upon the patient's metabolic requirements. When the patient's heart rate increases or when the pacemaker increases the pacing rate, pacemaker syndrome may appear.

One scenario that may lead to pacemaker syndrome is the situation when the patient's intrinsic ventricular activation occurs a long time after the patient's intrinsic or paced atrial activation. A long delay between atrial activation and ventricular activation causes the T-wave to be delayed, and increases the risk that the P-wave of the succeeding cardiac cycle will be superimposed on the T-wave. When the heart rate of the patient is elevated and the cardiac cycles shorten, the risk of superposition increases, and therefore so does the risk of pacemaker syndrome.

The invention provides for pacing the heart to reduce the risk of pacemaker syndrome. One pacing technique is to apply ventricular paces, thereby reducing the delay between the atrial activation and the ventricular activation, and thereby causing the T-wave to occur sooner. Another technique, available to a patient who receives atrial pacing, is to decrease the atrial pacing rate.

In one embodiment, the invention is directed to a method comprising determining a risk of pacemaker syndrome and pacing a heart to reduce the risk of the pacemaker syndrome when the risk exceeds a risk threshold. The method may also include measuring a heart rate and determining the risk of pacemaker syndrome when the measured heart rate exceeds a rate threshold.

In another embodiment, the invention is directed to a computer-readable medium containing instructions that cause a programmable processor to carry out the above method.

In a further embodiment, the invention presents a device comprising a lead having at least one electrode deployed proximate to a heart, a pulse generator to generate at least one pacing stimulus to pace the heart via the electrode and a processor. The processor determines a risk of pacemaker syndrome, and controls the pulse generator to pace the heart to reduce the risk of the pacemaker syndrome when the risk exceeds a risk threshold.

The details of one or more embodiments of the invention are set forth in the accompanying drawings and the description below. Other features, objects, and advantages of the invention will be apparent from the description and drawings, and from the claims.

DETAILED DESCRIPTION OF THE INVENTION

Figure 1:
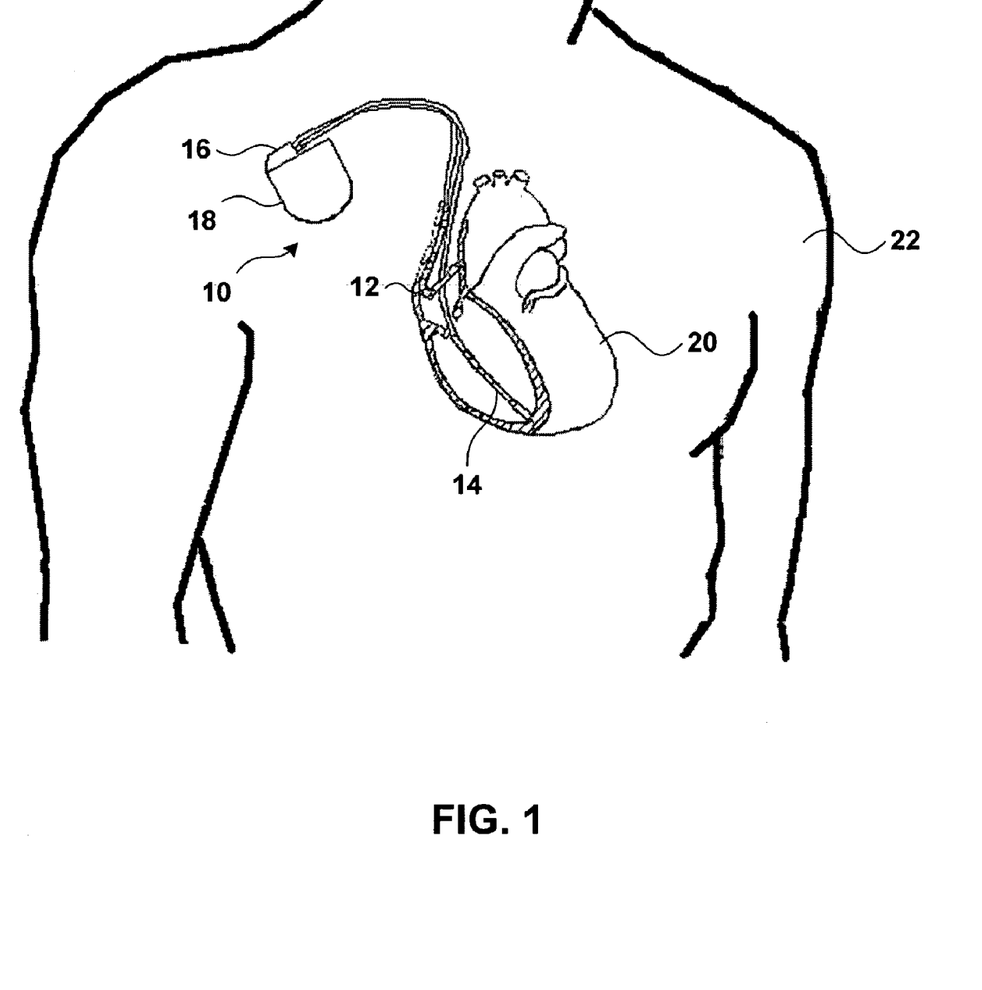
FIG. 1 is a schematic view of an exemplary implantable medical device that may practice the invention.

FIG. 1 is a schematic view of one embodiment of a device that may practice the invention. Implantable medical device ("IMD") 10 is a pacemaker comprising at least one atrial pacing and sensing lead 12 and at least one ventricular pacing and sensing lead 14 attached to connector module 16 of hermetically sealed enclosure 18 and implanted near human or mammalian heart 20 of a patient 22. Pacing and sensing leads 12 and 14 sense electrical signals attendant to the depolarization and repolarization of the heart 20, and further provide pacing pulses for causing depolarization of cardiac tissue in the vicinity of the distal ends thereof. Leads 12 and 14 may have unipolar or bipolar electrodes disposed thereon.

IMD 10 is one example of a device that may practice the invention. In particular, IMD 10 is an example of a device that has the capability of detecting and addressing pacemaker syndrome. In particular, IMD 10 has the capability to detect electrical signals generated by heart 20, and further has the capability to determine whether the signals indicate pacemaker syndrome. IMD 10 further has the capability to adjust pacing to alleviate pacemaker syndrome and restore a satisfactory atrioventricular sequence.

The invention is not limited to application with a dual-chamber pacemaker such as IMD 10, however. The invention may be applied to a variety of external or implantable devices, including single-chamber, three-chamber and four-chamber pacemakers.

Figure 2:
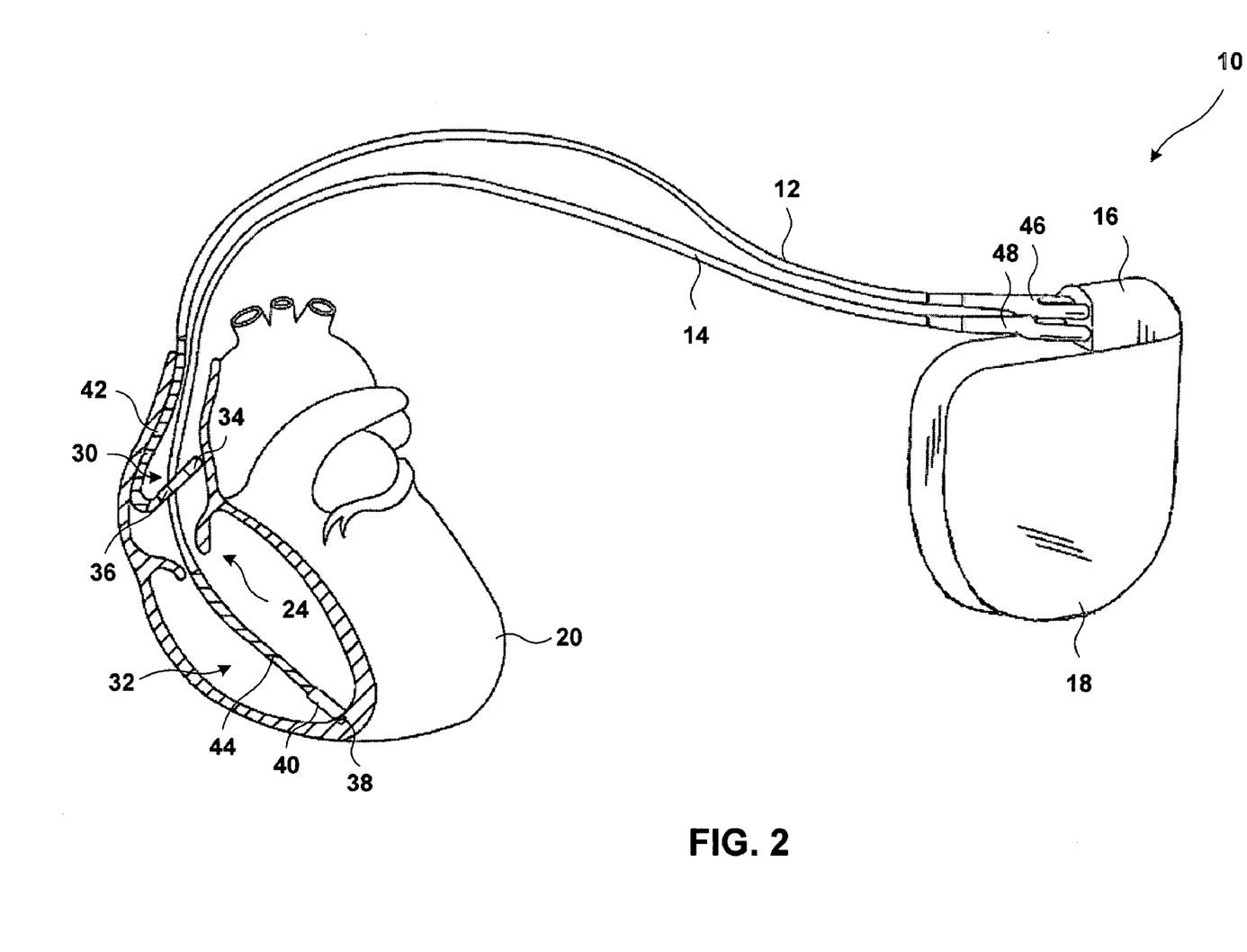
FIG. 2 shows the implantable medical device located in and near a heart.

FIG. 2 shows IMD 10, with connector module 16 and hermetically sealed enclosure 18 located in and near human or mammalian heart 20. Ventricular pacing lead 14 extends from connector module 16 through right atrioventricular valve 24 to the right ventricle 32 of heart 20, and atrial pacing lead 12 extends from connector module 16 to the right atrium 30 of heart 20.

Atrial electrodes 34 and 36 disposed at the distal end of atrial pacing lead 12 are deployed in right atrium 30. Ventricular electrodes 38 and 40 disposed at the distal end of ventricular pacing lead 14 are deployed in right ventricle 32. Electrodes 34, 36, 38, 40 are used to sense electrical activity of heart 20, including atrial and ventricular depolarizations. Electrodes 34, 36, 38, 40 are also used to deliver paces to the right atrium 30 or right ventricle 32. Pulse generators (not shown in FIG. 2) inside enclosure 18 generate pacing pulses, which are transmitted along leads 12, 14 to electrodes 34, 36, 38, 40.

In addition to pacing, IMD 10 may apply other forms of therapy to address various cardiac problems. In FIG. 2, for example, electrodes 34, 36, 38, 40 may be used to apply paces to treat various forms of tachycardia, and atrial lead 12 and ventricular lead 14 include defibrillation electrodes 42 and 44. Defibrillation electrodes 42 and 44 deliver defibrillation shocks to right atrium 30 or right ventricle 32.

Atrial and ventricular leads 12, 14 each include an elongated insulative lead body carrying one or more conductors insulatively separated from one another. At the proximal end of leads 12, 14 are bifurcated connectors 46, 48, which electrically couple the connectors to connector module 16 of IMD 10.

Figure 3:
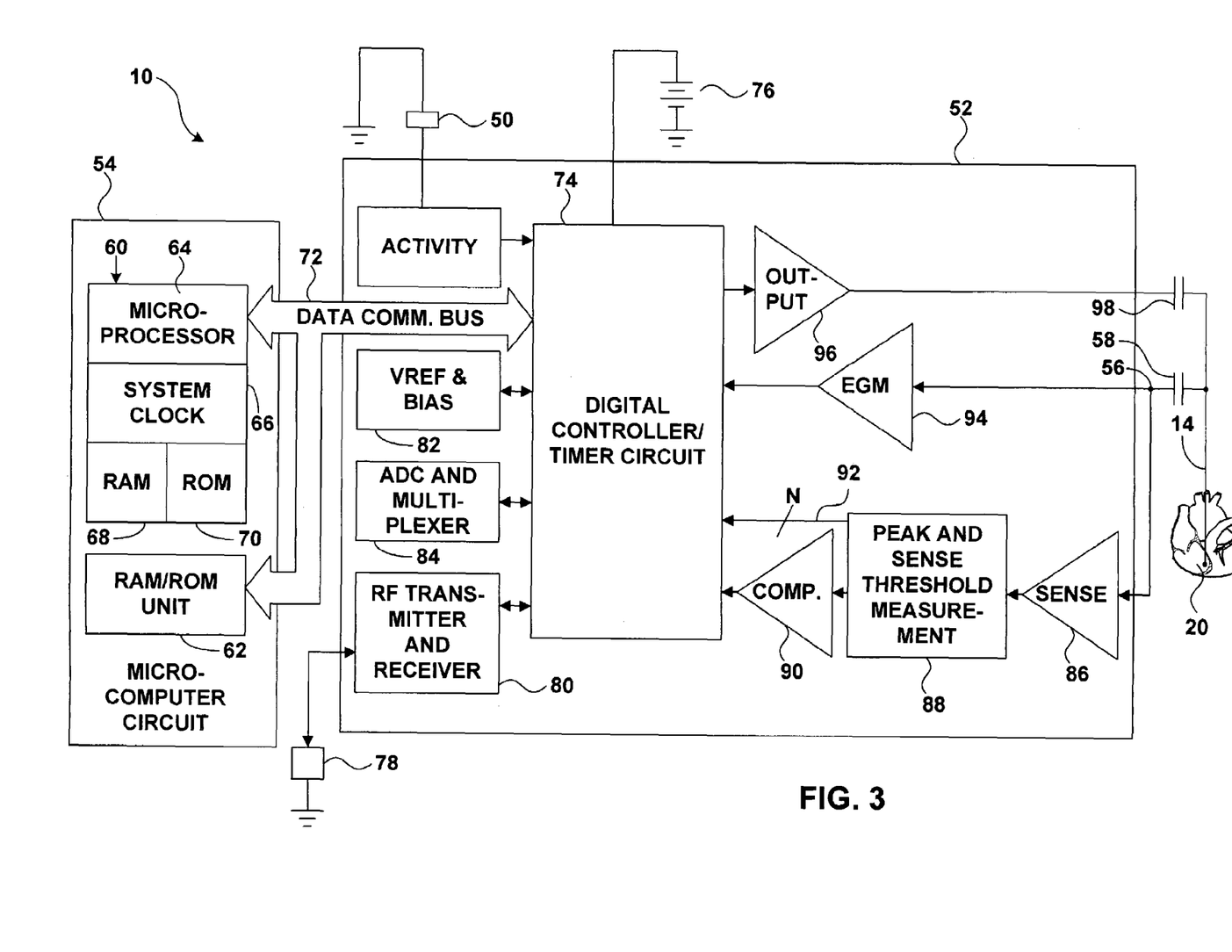
FIG. 3 is a block diagram illustrating the constituent components of the implantable medical device of FIGS. 1 and 2.

FIG. 3 shows a block diagram illustrating the constituent components of IMD 10 in accordance with one embodiment of the invention, in which IMD 10 is a pacemaker having a microprocessor-based architecture. IMD 10 includes one or more activity sensors 50. Activity sensor 50 may include an accelerometer, such as an electrostatic accelerometer, a piezoceramic accelerometer or a microelectromechanical accelerometer, that typically provides a sensor output that varies as a function of a measured parameter relating to a patient's metabolic requirements. In other words, activity sensor 50 detects motion of patient 22 that accompanies physical activity, and IMD 10 may adjust the pacing rate to the metabolic needs associated with the physical activity.

As will be discussed below, changes in the patient's physical activity or adjustments to the pacing rate may cause pacemaker syndrome to develop. When the patient experiences a low level of activity with a low heart rate, the patient may be at little risk of pacemaker syndrome. When the patient's level of activity causes his heart rate to rise, however, pacing may cause the atria and the ventricles to activate at approximately the same time, and the patient consequently develops pacemaker syndrome.

The output of activity sensor 50 is coupled to input/output circuit 52. Input/output circuit 52 contains analog circuits for interfacing with heart 20, activity sensor 50, and other components and circuits for the application of stimulating pulses to heart 20. The rate of heart 20 is controlled by software-implemented algorithms stored within microcomputer circuit 54.

For the sake of convenience, IMD 10 in FIG. 3 is shown with only lead 14 connected. Similar circuitry and connections not explicitly shown in FIG. 3 apply to lead 12 (shown in FIGS. 1 and 2), however. Lead 14 is coupled to node 56 in IMD 10 through input capacitor 58.

Microcomputer circuit 54 comprises on-board circuit 60 and off-board circuit 62. On-board circuit 60 includes microprocessor 64, system clock circuit 66 and on-board random access memory (RAM) 68 and read-only memory (ROM) 70. Off-board circuit 62 comprises a RAM/ROM unit. On-board circuit 60 and off-board circuit 62 are each coupled by data communication bus 72 to digital controller/timer circuit 74. Microcomputer circuit 54 may comprise a custom integrated circuit device augmented by standard RAM/ROM components.

Electrical components shown in FIG. 3 are powered by an appropriate implantable battery power source 76. For the sake of clarity, the coupling of battery power to the various components of IMD 10 is not shown in FIG. 3.

Antenna 78 is connected to input/output circuit 52 to permit uplink/downlink telemetry through radio frequency (RF) transmitter and receiver telemetry unit 80. IMD 10 in FIG. 3 is programmable by an external programming unit (not shown in the figures) that communicates with IMD 10 via antenna 78 and RF transmitter and receiver telemetry unit 80.

VREF and bias circuit 82 generates stable voltage reference and bias currents for analog circuits included in input/output circuit 52. Analog-to-digital converter (ADC) and multiplexer unit 84 digitizes analog signals and voltages to provide "real-time" telemetry intracardiac signals and battery end-of-life (EOL) replacement functions. Operating commands for controlling the timing of IMD 10 are coupled from microprocessor 64 via data bus 72 to digital controller/timer circuit 74, where digital timers and counters establish the overall escape interval of the IMD 10 as well as various refractory, blanking and other timing windows for controlling the operation of peripheral components disposed within input/output circuit 52.

Digital controller/timer circuit 74 is coupled to sensing circuitry, including sense amplifier 86, peak sense and threshold measurement unit 88 and comparator/threshold detector 90. Sense amplifier 86 amplifies electrical cardiac signals sensed via lead 14 and provides an amplified signal to peak sense and threshold measurement circuitry 88, which in turn provides an indication of peak sensed voltages and measured sense amplifier threshold voltages on multiple conductor signal path 92 to digital controller/timer circuit 74. An amplified sense amplifier signal is also provided to comparator/threshold detector 90.

Digital controller/timer circuit 74 is further coupled to electrogram (EGM) amplifier 94 for receiving amplified and processed signals sensed by lead 14. The electrogram signal provided by EGM amplifier 94 is employed, for example, when IMD 10 is being interrogated by an external programmer to transmit a representation of a cardiac analog electrogram. Output pulse generator 96 provides amplified pacing stimuli to heart 20 through coupling capacitor 98 in response to a pacing trigger signal provided by digital controller/timer circuit 74.

Sensing circuitry and digital controller/timer circuit 74 cooperate to sense or control various timing intervals. One such sensed interval is the P-R interval, i.e., the interval between an intrinsic atrial activation and an intrinsic ventricular activation. A related sensed interval is the interval between a paced atrial activation and an intrinsic ventricular activation, which will be called the A-R interval to distinguish it from the P-R interval.

Another sensed interval of interest is the R-R interval, which is the interval between successive intrinsic ventricular activations. The R-R interval is related to the intrinsic heart rate of the patient. In particular, as the intrinsic heart rate increases, the R-R interval becomes shorter, and vice versa. As will be described below, IMD 10 uses the heart rate of the patient as a parameter for detecting and addressing pacemaker syndrome. IMD 10 may measure the heart rate by sensing the R-R interval. IMD 10 may also sense the P-P interval or other intervals between comparable events in succeeding cardiac cycles, and measure the heart rate by sensing any of those other intervals.

Other sensed intervals of interest include the Q-T interval and the T-P interval. The Q-T interval represents the interval between sensed or paced ventricular activation and ventricular repolarization. The T-P interval represents the interval between ventricular repolarization and a subsequent atrial activation. As will be described in more detail below, one technique for detecting pacemaker syndrome includes pacing a ventricle, measuring the subsequent Q-T interval, and using the measured Q-T interval to compute the T-P interval.

The P-wave accompanies atrial activation, and occurs before and during atrial contraction. The T-wave begins during ventricular contraction and continues through ventricular relaxation. When the P-wave is superimposed on the T-wave, there is an increased likelihood that atrial activation is occurring at substantially the same time as a ventricular activation. Pacemaker syndrome may be the result. The T-wave and P-waves are superimposed when the T-wave and P-wave overlap, or when the T-wave precedes the P-wave by a short time interval, such as 100 milliseconds.

Digital controller/timer circuit 74 further controls various timing intervals for delivery of paces. One such controlled interval is the A-V interval, which represents the interval between a paced or sensed atrial activation and a scheduled ventricular pace. In some patients, the A-V interval is programmed to be long enough to give heart 20 an opportunity to have an intrinsic ventricular contraction. When the ventricular contraction happens on its own before the expiration of the A-V interval, the scheduled ventricular pace for that cardiac cycle is inhibited. When the ventricular contraction fails to take place before the expiration of the A-V interval, IMD 10 delivers the scheduled ventricular pace. As will be described below, one technique for addressing pacemaker syndrome is to adjust the A-V interval. Another controlled interval is the A-A interval, which represents the interval between successive atrial paces.

Figure 4:
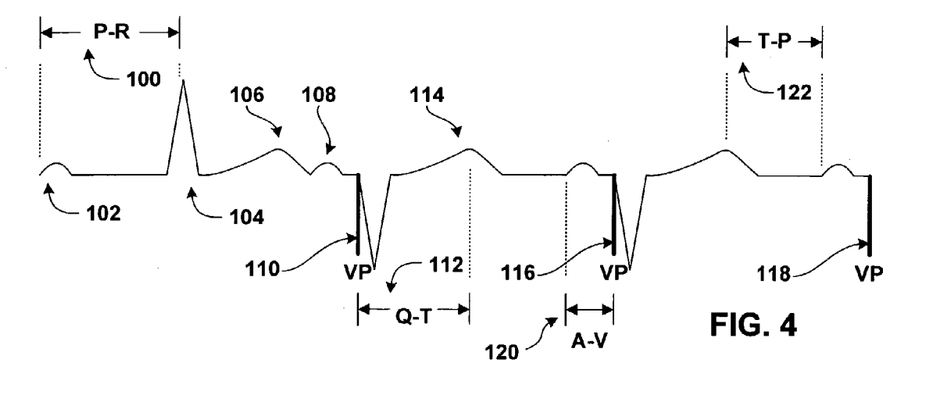
FIG. 4 is a timing diagram of an electrogram that illustrates the application of one embodiment of the invention.

FIG. 4 is a timing diagram of an EGM that illustrates one embodiment and application of the invention. The EGM is from a patient having an implantable device such as IMD 10. In FIG. 4, the patient exhibits a long P-R interval 100, i.e., a long interval between an intrinsic atrial activation, as indicated by P-wave 102, and an intrinsic ventricular activation, as indicated by R-wave 104. The T-wave 106 following R-wave 104 is followed very closely by a P-wave 108 of a subsequent cardiac cycle. The closeness of T-wave 106 and P-wave 108 suggests that atrial and ventricular activations are occurring at substantially the same time, causing pacemaker syndrome.

When the patient's heart beats at a normal rate, a long P-R interval is not necessarily going to cause a risk of pacemaker syndrome. When the patient's heart rate increases, however, a long P-R interval may delay the ventricular activation, and thus delay the T-wave to the point that the T-wave and the P-wave of the subsequent cycle are close to one another. In other words, the risk of pacemaker syndrome increases with an increase in heart rate.

Accordingly, when the patient's heart rate reaches a certain threshold, such as 100 beats per minute, IMD 10 performs a test to determine whether the patient is at risk of pacemaker syndrome. In particular, IMD 10 delivers a ventricular pace 110 shortly after P-wave 108, and measures the Q-T interval 112 that follows. In some embodiments of the invention, a Q-T interval is best measured following a ventricular pace, rather than following an intrinsic ventricular activation. In general, a Q-T interval following a ventricular pace is comparable to a Q-T interval following an intrinsic ventricular activation.

Measured Q-T interval 112 represents the time interval between the ventricular activation and the following T-wave 114. By computing the time of the T-wave 114, and by measuring the heart rate and P-R interval 100, IMD 10 computes whether the patient is at risk of atrial and ventricular activations occurring at substantially the same time. In particular, IMD 10 computes the T-P interval between intrinsic ventricular and atrial activations, such as activations reflected by T-wave 106 and P-wave 108. IMD 10 may determine that the patient is at risk of atrial and ventricular activations occurring at substantially the same time when the T-P interval between intrinsic ventricular and atrial activations is small.

IMD 10 may compute the estimated T-P interval between intrinsic ventricular and atrial activations from the heart rate, measured P-R interval 100 and measured Q-T interval 112. From the heart rate, IMD 10 computes the P-P interval, and subtracts P-R interval 100 and Q-T interval 112. The difference is the estimated T-P interval. When the estimated T-P interval is less than some threshold interval, such as 100 milliseconds, the patient is at risk of pacemaker syndrome.

To address the risk of pacemaker syndrome, IMD 10 begins delivering ventricular paces 116, 118. IMD 10 may, in one embodiment, shorten the A-V interval 120, in effect scheduling ventricular paces to occur more quickly after intrinsic atrial activations. If the patient has a long P-R interval, then the scheduled ventricular paces will occur before the intrinsic ventricular activations, and IMD 10 will deliver ventricular paces 116, 118 rather than waiting for intrinsic ventricular activation. In response to ventricular pacing, the patient's T-P interval 122 increases, thereby reducing the risk of pacemaker syndrome. Ventricular pacing may be discontinued when the patient's heart rate falls below a threshold, such as 100 beats per minute.

Figure 5:
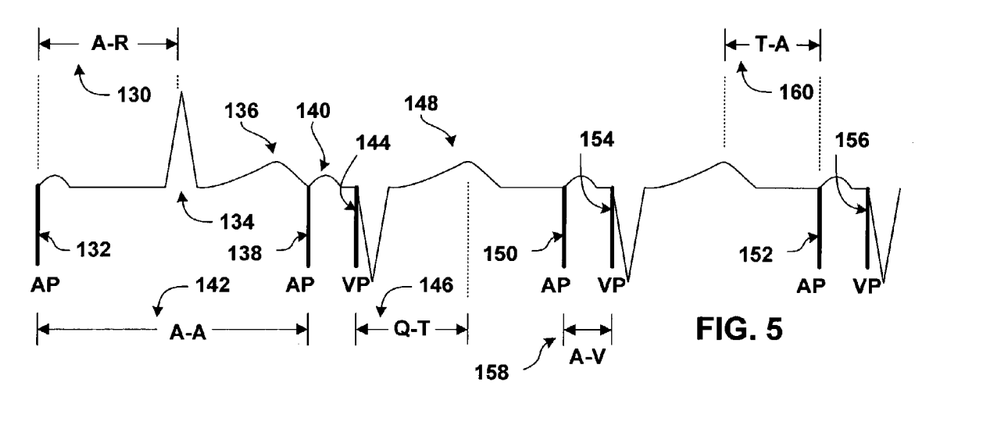
FIG. 5 is a timing diagram of an electrogram that illustrates application of another embodiment of the invention.

FIG. 5 is a timing diagram of an EGM that illustrates another embodiment and application of the invention. The EGM is from a patient having an implantable device such as IMD 10. In FIG. 5, the patient exhibits a long A-R interval 130, i.e., a long interval between an atrial pace 132 and an intrinsic ventricular activation, as indicated by R-wave 134. The T-wave 136 following R-wave 134 is followed very closely by an atrial pace 138, which causes P-wave 140 of a subsequent cardiac cycle. As in FIG. 4, the closeness of T-wave 136 and P-wave 140 suggests that atrial and ventricular activations are occurring at substantially the same time, causing pacemaker syndrome.

When IMD 10 paces the patient's heart beats at a normal rate, a long A-R interval is not necessarily going to cause a risk of pacemaker syndrome. IMD 10 may, however, shorten the A-A interval 142, i.e., the interval between successive atrial paces 132 and 138. IMD 10 may shorten the A-A interval in response to a change in the metabolic needs of the patient, such as a change in physical activity detected by activity sensor 50. When IMD 10 paces the heart at a more rapid rate, a long A-R interval may delay the ventricular activation, and thus delay the T-wave to the point that the T-wave and the atrial pace or P-wave of the subsequent cycle are close to one another. As with the example depicted in FIG. 4, the risk of pacemaker syndrome increases with an increase in heart rate.

Accordingly, when the patient's paced heart rate reaches a certain threshold, such as 100 beats per minute, IMD 10 performs a test to determine whether the patient is at risk of pacemaker syndrome. The threshold may also be expressed in terms of a time interval, e.g., when the patient's A-A interval falls below 600 milliseconds, IMD 10 performs the test to determine whether the patient is at risk of pacemaker syndrome.

The test for pacemaker syndrome is similar to the test described above in connection with FIG. 4. In particular, IMD 10 delivers a ventricular pace 144 shortly after atrial pace 138, and measures the Q-T interval 146 that follows. By computing the time of the T-wave 148, by controlling A-A interval 142, and by measuring A-R interval 130, IMD 10 computes whether the patient is at risk of atrial and ventricular activations occurring at substantially the same time. In particular, IMD 10 subtracts A-R interval 100 and measured Q-T interval 146 from A-A interval 130. The difference is the estimated T-A interval, i.e., the estimated time between the T-wave resulting from an intrinsic ventricular activation and a subsequent atrial pace. When the estimated T-A interval is less than some threshold interval, such as 100 milliseconds, the patient is at risk of pacemaker syndrome.

To address the risk of pacemaker syndrome, IMD 10 continues delivering atrial paces 150, 152, and begins delivering ventricular paces 154, 156 after atrial paces 150, 152. In one embodiment, IMD 10 shortens the A-V interval 158, so that ventricular paces are scheduled more quickly after atrial paces. If the patient has a long A-R interval, then the scheduled ventricular paces will occur before the intrinsic ventricular activations. In response to coordinated atrial and ventricular pacing, the patient's T-A interval 160 increases, thereby reducing the risk of pacemaker syndrome. Ventricular pacing may be discontinued when the patient's heart rate falls below a threshold, such as 100 beats per minute, i.e., ventricular pacing may be discontinued when the A-A interval rises above 600 milliseconds.

Figure 6:
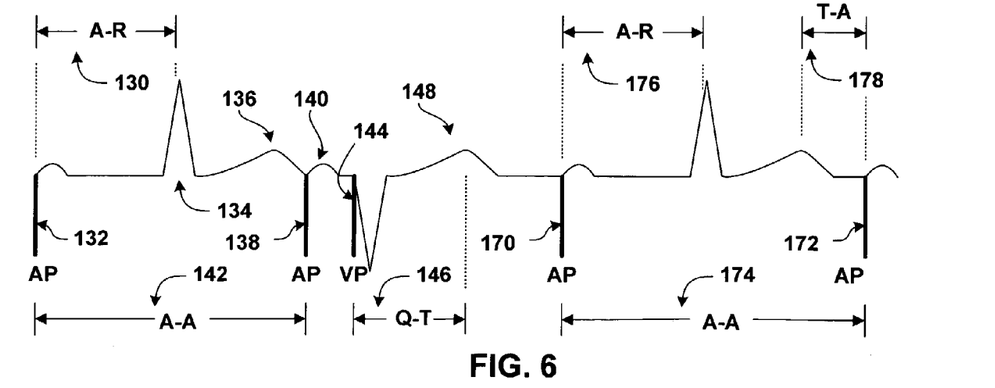
FIG. 6 is a timing diagram of an electrogram that illustrates application of a further embodiment of the invention.

FIG. 6 is a timing diagram of an EGM that illustrates another embodiment and application of the invention. The EGM is from a patient having an implantable device such as IMD 10. The risk of pacemaker syndrome in FIG. 6 is the same as that depicted in FIG. 5, but IMD 10 addresses the risk in a different way.

In particular, the patient in FIG. 6 receives atrial pacing and exhibits a long A-R interval 130. As a result, T-wave 136 is followed very closely by atrial pace 138, indicating a risk of pacemaker syndrome. The risk may be present when the patient's paced heart rate reaches a certain threshold, such as 100 beats per minute. When the threshold is surpassed, IMD 10 performs a test to determine whether the patient is at risk of pacemaker syndrome. As in FIG. 5, IMD 10 delivers a ventricular pace 144 shortly after atrial pace 138, and measures the Q-T interval 146 that follows, and uses measure Q-T interval 146 to estimate the T-A interval. When the estimated T-A interval is less than some threshold interval, such as 100 milliseconds, the patient is at risk of pacemaker syndrome.

To address the risk of pacemaker syndrome, IMD 10 continues delivering atrial paces 170, 172, but increases the A-A interval 174 between the atrial paces. In other words, IMD 10 decreases the atrial pacing rate. IMD 10 does not perform ventricular pacing and, as a result, the A-R interval 176 remains substantially unchanged. Because of the increased A-A interval 174, however, the T-A interval 178 is increased and the risk of pacemaker syndrome is reduced.

Figure 7:
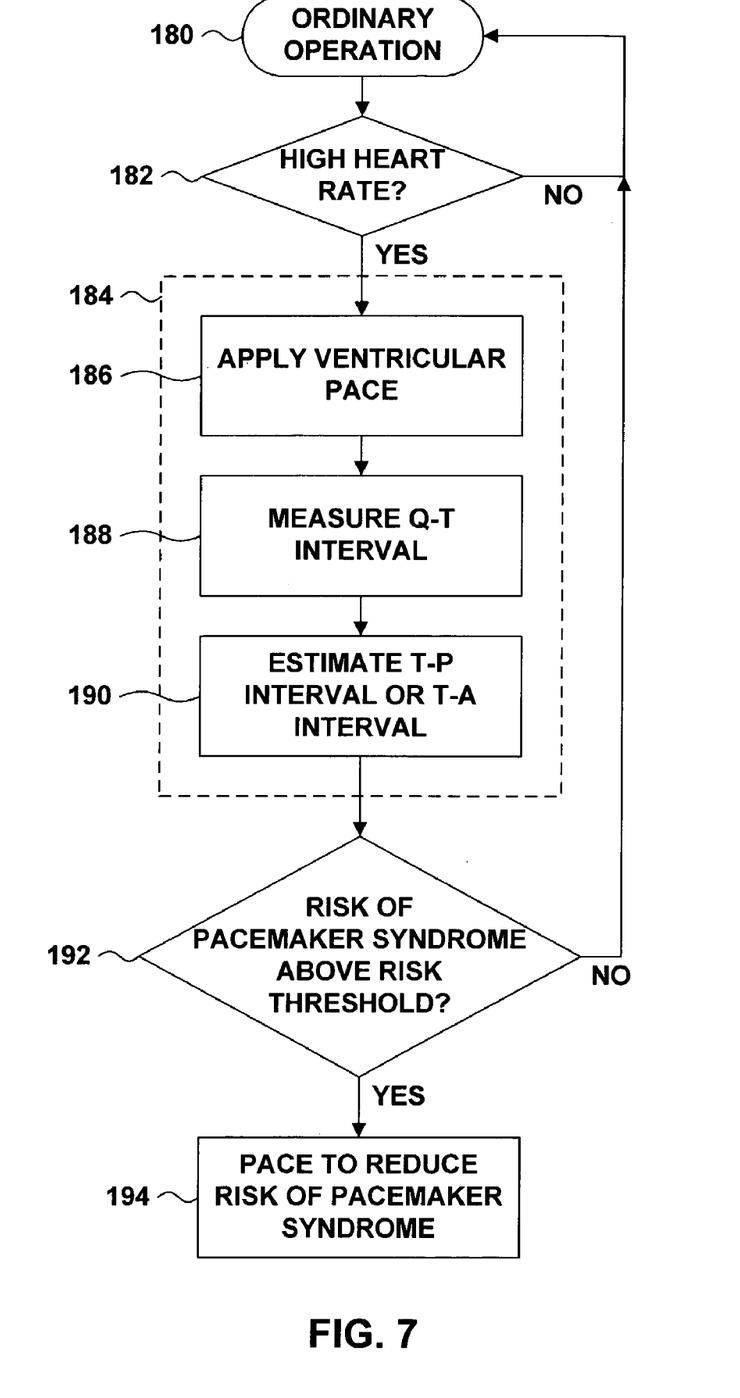
FIG. 7 is a flow diagram illustrating techniques for detecting and addressing pacemaker syndrome.

FIG. 7 is a flow diagram illustrating a technique for carrying out the invention that may be practiced by an implantable medical device such as IMD 10. It is assumed that IMD 10, when operating under ordinary conditions (180), does not produce pacemaker syndrome. A risk of pacemaker syndrome may arise, however, when the patient's heart rate is high (182).

In general, determining whether the heart rate is high (182) comprises measuring the heart rate and comparing the measured heart rate to a rate threshold. When the measured heart rate exceeds the rate threshold, IMD 10 takes action to determine a risk of pacemaker syndrome (184). IMD 10 may measure heart rate by any of several procedures. For example, IMD 10 may compute a measure of the heart rate by measuring any interval that defines a cardiac cycle, such as a P-P interval or an R-R interval. IMD 10 may also compute a measure of the heart rate from a pacing rate or pacing interval controlled by IMD 10, such as the atrial pacing rate or the A-A interval.

An exemplary rate threshold is 100 beats per minute. IMD 10 may be programmed, however, to apply any rate threshold.

IMD 10 determines a risk of pacemaker syndrome (184) by any algorithm. One technique for determining a risk of pacemaker syndrome is to apply a ventricular pace (186) and, by sensing the time between the ventricular pace and the resulting T-wave, measure the Q-T interval (188). IMD 10 uses the Q-T interval measurement to estimate the T-P interval or the T-A interval (190). The T-P or T-A interval reflects whether a ventricular activation and a subsequent atrial activation are close in time to one another, and thus reflects the risk of pacemaker syndrome.

As described above in connection with FIG. 4, an observed P-P interval, minus an observed P-R interval, minus the measured Q-T interval yields an estimate of the T-P interval. As described above in connection with FIGS. 5 and 6, an A-A interval, minus an observed A-R interval, minus the measured Q-T interval yields an estimate of the T-A interval.

IMD 10 compares the risk of pacemaker syndrome to a risk threshold (192). This comparison may be accomplished by comparing the estimated T-P interval or T-A interval to a threshold time. When, for example, the estimated T-P interval or T-A interval is 100 milliseconds or less, then IMD 10 may determine that the risk of pacemaker syndrome exceeds the risk threshold. IMD 10 may be programmed, however, to apply any risk threshold.

When the risk of pacemaker syndrome exceeds the risk threshold, IMD 10 paces the heart to reduce the risk of pacemaker syndrome (194). The actual pacing therapy that IMD 10 applies depends upon the circumstances. When a patient's atria activate intrinsically and the patient has a long P-R interval, as illustrated in FIG. 4, IMD 10 may reduce the risk of pacemaker syndrome by ventricular pacing. In particular, IMD 10 may shorten the A-V interval so that ventricular activation is more likely to be paced and less likely to be intrinsic. As a result, ventricular activation occurs sooner and the patient's T-P interval increases, thereby reducing the risk of pacemaker syndrome.

When a patient's atria are paced and the patient has a long A-R interval, as illustrated in FIGS. 5 and 6, IMD 10 may reduce the risk of pacemaker syndrome by at least two distinct procedures. One procedure, illustrated in FIG. 5, involves ventricular pacing in addition to atrial pacing. Another procedure, illustrated in FIG. 6, involves atrial pacing only, but at a reduced atrial pacing rate. Both procedures increase the patient's T-A interval, thereby reducing the risk of pacemaker syndrome.

The invention is not limited to these particular procedures. Other situations may arise that may put a patient at risk of pacemaker syndrome. Whenever the T-wave occurs substantially at the same time as, or after, the P-wave, the atrial and ventricular activations overlap, and pacemaker syndrome results. IMD 10 may determine a risk of pacemaker syndrome associated with these situations, comparing the risk to a risk threshold, and, when the risk exceeds the risk threshold, pace one or more chambers of the heart to reduce the risk of the pacemaker syndrome. In general, IMD 10 applies pacing stimuli to control atrial activations, ventricular activations, or both, to cause the T-wave to occur substantially before the next P-wave.

In general, when the risk of pacemaker syndrome is no longer present, pacing to reduce the risk of the pacemaker syndrome may be discontinued. For example, when the heart rate of the patient drops below the rate threshold, the risk of pacemaker syndrome may no longer be present, and ventricular pacing to shorten the time between atrial and ventricular activations may be discontinued. In particular, the IMD may increase the A-V interval to schedule ventricular paces to occur later after intrinsic atrial activations, and allowing a greater opportunity for intrinsic ventricular activation.

The invention may offer one or more advantages. It is not necessary to address pacemaker syndrome by continually applying both atrial and ventricular pacing. Rather, atrial pacing, or ventricular pacing, or both, can be selectively applied to reduce the risk of pacemaker syndrome. In the scenario depicted in FIG. 4, pacemaker syndrome was addressed with ventricular pacing to shorten the time between atrial and ventricular activations. In the scenario depicted in FIG. 5, pacemaker syndrome was addressed with both atrial and ventricular pacing, with ventricular pacing shortening the time between atrial and ventricular activations. In the scenario depicted in FIG. 6, pacemaker syndrome was addressed with atrial pacing at a slower rate.

By not continually applying both atrial and ventricular pacing, the invention preserves intrinsic activation where appropriate. In general, it is desirable for the chambers of the heart to activate of their own accord, and to pace a chamber only when necessary. Various embodiments of the invention preserve intrinsic activation. In some embodiments, the patient receives no pacing until the risk of pacemaker syndrome is present. In other embodiments, the patient receives pacing to a single chamber until the risk of pacemaker syndrome is present, and then the patient receives pacing to at least one additional chamber.

A number of embodiments of the invention have been described. However, one skilled in the art will appreciate that the invention can be practiced with embodiments other than those disclosed. For example, the invention may be practiced in devices other than the specific devices described herein. Furthermore, the pacing techniques that are applied to reduce pacemaker syndrome, may be customized to a particular patient. The various thresholds described herein, such as the risk threshold and the rate threshold, may also be customized to a particular patient.

Furthermore, the techniques of the invention may cooperate with other pacing techniques, such as antitachycardia pacing and cardiac resynchronization. The techniques of the invention do not foreclose the application of other pacing strategies.

The invention may be embodied as a computer-readable medium that includes instructions for causing a programmable processor, such as microcomputer circuit 54 in FIG. 3, to carry out the methods described above. A "computer-readable medium" includes but is not limited to read-only memory, Flash memory and a magnetic or optical storage medium. The instructions may be implemented as one or more software modules, which may be executed by themselves or in combination with other software. These and other embodiments are within the scope of the following claims.

The invention claimed is:

1. A method comprising:
   determining a risk of pacemaker syndrome;
   pacing a heart to reduce the risk of the pacemaker syndrome when the risk exceeds a risk threshold; and
   estimating an interval between a T-wave and a succeeding atrial activation; and
   determining that the risk of the pacemaker syndrome exceeds the risk threshold when the interval is below an interval threshold.

2. The method of claim 1, wherein determining the risk of pacemaker syndrome comprises:
   measuring a heart rate; and
   determining the risk of pacemaker syndrome when the measured heart rate exceeds a rate threshold.

3. The method of claim 2, wherein measuring a heart rate comprises measuring one of a P-P interval between successive intrinsic atrial activations, an R-R interval between successive intrinsic ventricular activations and an A-A interval between successive atrial paces.

4. The method of claim 2, wherein the rate threshold is approximately 100 beats per minute.

5. The method of claim 1, wherein the interval threshold is approximately 100 milliseconds.

6. The method of claim 1, wherein pacing the heart to reduce the risk of the pacemaker syndrome comprises decreasing an A-V interval that defines the interval between an atrial event and a scheduled ventricular pace.

7. The method of claim 1, wherein pacing the heart to reduce the risk of the pacemaker syndrome comprises decreasing an atrial pacing rate.

8. The method of claim 1, wherein pacing the heart to reduce the risk of the pacemaker syndrome comprises pacing the heart to cause a T-wave in a first cardiac cycle to occur substantially ahead of a P-wave in a successive cardiac cycle.

9. A method comprising:
   determining a risk of pacemaker syndrome by estimating a time of occurrence of a T-wave and a time of occurrence of a succeeding atrial activation;
   determining that the risk of the pacemaker syndrome exceeds a risk threshold when the T-wave and the atrial activation occur at substantially the same time; and
   pacing a heart to reduce the risk of the pacemaker syndrome when the risk exceeds the risk threshold.

10. A method comprising:
    determining a risk of pacemaker syndrome by measuring a Q-T interval;
    estimating one of a T-P interval and a T-A interval as a function of the measured Q-T interval; and
    pacing a heart to reduce the risk of the pacemaker syndrome when the determined risk exceeds a risk threshold.

11. The method of claim 10, wherein measuring the Q-T interval comprises:
    delivering a ventricular pace; and
    measuring the time interval between the ventricular pace and a T-wave.

12. A computer-readable medium comprising instructions for causing a programmable processor to:

determine a risk of pacemaker syndrome;
pace a heart to reduce the risk of the pacemaker syndrome when the risk exceeds a risk threshold;
estimate an interval between a T-wave and a succeeding atrial activation; and
determine that the risk of the pacemaker syndrome exceeds the risk threshold when the interval is below an interval threshold.

13. The medium of claim 12, wherein the instructions causing the processor to determine a risk of pacemaker syndrome cause the processor to:
measure a heart rate; and
determine the risk of pacemaker syndrome when the measured heart rate exceeds a rate threshold.

14. The medium of claim 13, wherein the instructions causing the processor to measure a heart rate comprise instructions causing the processor to measure one of a P-P interval between successive intrinsic atrial activations, an R-R interval between successive intrinsic ventricular activations and an A-A interval between successive atrial paces.

15. The medium of claim 13, wherein the rate threshold is approximately 100 beats per minute.

16. The medium of claim 12, wherein the interval threshold is approximately 100 milliseconds.

17. The medium of claim 12, wherein the instructions causing the processor to pace the heart to reduce the risk of the pacemaker syndrome comprise instructions causing the processor to decrease an A-V interval that defines the interval between an atrial event and a scheduled ventricular pace.

18. The medium of claim 12, wherein the instructions causing the processor to pace the heart to reduce the risk of the pacemaker syndrome comprise instructions causing the processor to decrease an atrial pacing rate.

19. The medium of claim 12, wherein the instructions causing the processor to pace the heart to reduce the risk of the pacemaker syndrome comprise instructions causing the processor to pace the heart to cause a T-wave in a first cardiac cycle to occur substantially ahead of a P-wave in a successive cardiac cycle.

20. A computer-readable medium comprising instructions for causing a programmable processor to:
determine a risk of pacemaker syndrome;
pace a heart to reduce the risk of the pacemaker syndrome when the risk exceeds a risk threshold;
estimate a time of occurrence of a T-wave and a time of occurrence of a succeeding atrial activation; and
determine that the risk of the pacemaker syndrome exceeds the risk threshold when the T-wave and the atrial activation occur at substantially the same time.

21. A computer-readable medium comprising instructions for causing a programmable processor to:
determine a risk of pacemaker syndrome;
pace a heart to reduce the risk of the pacemaker syndrome when the risk exceeds a risk threshold;
measure a Q-T interval; and
estimate one of a T-P interval and a T-A interval as a function of the measured Q-T interval.

22. The medium of claim 21, wherein the instructions causing the processor to measure the Q-T interval comprise instructions causing the processor to:
deliver a ventricular pace; and
measure the time interval between the ventricular pace and a T-wave.

23. A device comprising:
a lead having at least one electrode deployed proximate to a heart;
a pulse generator to generate at least one pacing stimulus to pace the heart via the electrode; and
a processor to determine a risk of pacemaker syndrome and to control the pulse generator to pace the heart to reduce the risk of the pacemaker syndrome when the risk exceeds a risk threshold, wherein the processor is further configured to estimate a time of occurrence of a T-wave and a time of occurrence of a succeeding atrial activation; and to determine that the risk of the pacemaker syndrome exceeds the risk threshold when the T-wave and the atrial activation occur at substantially the same time.

24. The device of claim 23, wherein the processor is further configured to control the pulse generator to pace the heart to reduce the risk of the pacemaker syndrome by decreasing an A-V interval that defines the interval between an atrial event and a scheduled ventricular pace.

25. The device of claim 23, wherein the processor is further configured to control the pulse generator to pace the heart to reduce the risk of the pacemaker syndrome by decreasing an atrial pacing rate.

26. The device of claim 23, wherein the processor is further configured to control the pulse generator to pace the heart to reduce the risk of the pacemaker syndrome by controlling the pulse generator to pace the heart to cause a T-wave in a first cardiac cycle to occur substantially ahead of a P-wave in a successive cardiac cycle.

27. The device of claim 23, wherein the device is an implantable pacemaker.

28. The device of claim 23, wherein the processor is further configured to measure a heart rate and to determining the risk of pacemaker syndrome when the measured heart rate exceeds a rate threshold.

29. The device of claim 23, wherein the lead is further configured to sense a depolarization via the electrode.

* * * * *

UNITED STATES PATENT AND TRADEMARK OFFICE
CERTIFICATE OF CORRECTION

PATENT NO. : 7,647,103 B2 Page 1 of 1
APPLICATION NO. : 10/422064
DATED : January 12, 2010
INVENTOR(S) : Giorgio Corbucci It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 1580 days.

Signed and Sealed this

Sixteenth Day of November, 2010

David J. Kappos
*Director of the United States Patent and Trademark Office*